US010267816B2

(12) United States Patent
Oonuma et al.

(10) Patent No.: US 10,267,816 B2
(45) Date of Patent: Apr. 23, 2019

(54) AUTOMATIC ANALYSIS DEVICE

(71) Applicant: HITACHI HIGH-TECHNOLOGIES CORPORATION, Tokyo (JP)

(72) Inventors: Mitsuru Oonuma, Tokyo (JP); Hiroyuki Noda, Tokyo (JP); Katsuhiro Kambara, Tokyo (JP); Hiroaki Sakai, Tokyo (JP)

(73) Assignee: Hitachi High-Technologies Corporation, Tokyo (JP)

( * ) Notice: Subject to any disclaimer, the term of this patent is extended or adjusted under 35 U.S.C. 154(b) by 207 days.

(21) Appl. No.: 15/326,769

(22) PCT Filed: Sep. 2, 2015

(86) PCT No.: PCT/JP2015/074987
§ 371 (c)(1),
(2) Date: Jan. 17, 2017

(87) PCT Pub. No.: WO2016/052063
PCT Pub. Date: Apr. 7, 2016

(65) Prior Publication Data
US 2017/0205436 A1 Jul. 20, 2017

(30) Foreign Application Priority Data
Sep. 30, 2014 (JP) ................... 2014-200522

(51) Int. Cl.
G01N 35/02 (2006.01)
F25D 25/00 (2006.01)
(Continued)

(52) U.S. Cl.
CPC .......... *G01N 35/025* (2013.01); *F25D 25/00* (2013.01); *G01N 2035/00435* (2013.01);
(Continued)

(58) Field of Classification Search
CPC ....... G01N 35/025; G01N 2035/00435; G01N 2035/00445; G01N 2035/041;
(Continued)

(56) References Cited

U.S. PATENT DOCUMENTS

2012/0301359 A1 11/2012 Kraemer et al.
2014/0295562 A1 10/2014 Wakamiya et al.
(Continued)

FOREIGN PATENT DOCUMENTS

EP 1225450 A1 7/2002
EP 1 914 555 A2 4/2008
(Continued)

OTHER PUBLICATIONS

Extended European Search Report received in corresponding European Application No. 15847562.4 dated May 28, 2018.
(Continued)

*Primary Examiner* — Benjamin R Whatley
(74) *Attorney, Agent, or Firm* — Mattingly & Malur, PC

(57) ABSTRACT

An automatic analysis device has a structure that allows the operator to add or replace a reagent. A reagent container loading portion has an opening through which a reagent container is adapted to be introduced into the device. A reagent container transport tool has a plurality of reagent container insertion slots and is movable up and down. A refrigerator to cool a plurality of reagent containers has an opening that allows the reagent container transport tool to pass therethrough. An elevating and lowering mechanism is configured to elevate or lower the reagent container transport tool. A reagent container loading portion has a plurality of guide grooves arranged radially on its lower surface in front of the opening that are adapted to guide a reagent container. The guide grooves communicate with the respec-
(Continued)

tive reagent container insertion slots arranged radially on the reagent container transport tool at an elevated position.

9 Claims, 10 Drawing Sheets

(51) Int. Cl.
*G01N 35/00* (2006.01)
*G01N 35/04* (2006.01)

(52) U.S. Cl.
CPC .............. *G01N 2035/00445* (2013.01); *G01N 2035/041* (2013.01); *G01N 2035/0443* (2013.01); *G01N 2035/0465* (2013.01); *G01N 2035/0496* (2013.01)

(58) Field of Classification Search
CPC ... G01N 2035/0443; G01N 2035/0465; G01N 2035/0496; F25D 13/062; F25D 13/04
See application file for complete search history.

(56) References Cited

U.S. PATENT DOCUMENTS

| | | | |
|---|---|---|---|
| 2015/0268259 A1* | 9/2015 | Gomm | G01N 35/025 436/43 |
| 2016/0263576 A1* | 9/2016 | Sattler | B01L 9/00 |

FOREIGN PATENT DOCUMENTS

| | | |
|---|---|---|
| EP | 3 037 825 A1 | 6/2016 |
| JP | 2003-262642 A | 9/2003 |
| JP | 2012-189611 A | 10/2012 |
| WO | 2011/012657 A1 | 2/2011 |

OTHER PUBLICATIONS

International Search Report of PCT/JP2015/074987 dated Nov. 24, 2015.

* cited by examiner

AUTOMATIC ANALYSIS DEVICE

TECHNICAL FIELD

The present invention relates to an automatic analysis device used for chemical analyses, such as biochemical analyses or immunoassays in clinical examination.

BACKGROUND ART

An automatic analysis device used for chemical analyses, such as a biochemical analyzer or an immunoassay analyzer, in clinical examination executes measurement by preparing a plurality of types of reagents in a reagent storage in accordance with items to be analyzed, and sucking a predetermined quantity of reagent from a reagent container in the reagent storage at a timing when the reagent is used, and then mixing the reagent with a sample. If the reagent stored in the reagent storage runs short during analysis, stopping the analysis at that stage and adding a reagent will reduce the efficiency of the analysis. Automatic analyzers are therefore designed so that if a shortage of reagent is likely, the device will warn the operator about the shortage, thus avoiding the situation that the operator will have to stop the device to add a reagent or replace the reagent with a new one during the analysis. Patent Document 1 describes an automatic analysis device with a configuration in which a loading system that permits reagent containers to be mounted therein is provided on a part of a fixed disk so that any of the reagent containers can be changed independently of the actuation status of the reagent fixed disk.

CITATION LIST

Patent Literature

Patent Literature 1: JP 2012-189611A

SUMMARY OF INVENTION

Technical Problem

An operation of mounting reagent containers to be replaced on the loading system is performed by the operator. Patent Document 1 does not particularly take into consideration the device structure for reliably and easily performing the operation of mounting reagent containers on the loading system.

It is an object of the present invention to provide an automatic analysis device with a structure that allows the operator to reliably and easily perform an operation of adding a reagent or replacing a reagent with a new one.

Solution to Problem

An automatic analysis device in accordance with the present invention includes a reagent container loading portion having an opening through which a reagent container is adapted to be introduced into the device; a reagent container transport tool having arranged radially thereon a plurality of reagent container insertion slots, the reagent container transport tool being configured to be movable up and down; a refrigerator having in its upper portion an opening that allows the reagent container transport tool to pass therethrough, the refrigerator being adapted to cool a plurality of reagent containers; and an elevating and lowering mechanism configured to elevate or lower the reagent container transport tool. The reagent container loading portion has a plurality of guide grooves arranged radially on its lower surface in front of the opening, each guide groove being adapted to guide a reagent container. The plurality of radially arranged guide grooves communicate with the respective slots arranged radially on the reagent container transport tool at an elevated position.

Advantageous Effects of Invention

According to the present invention, it is possible to allow the operator to reliably and easily perform an operation of adding a reagent or replacing a reagent with a new one.

Other problems, configurations, and advantageous effects will become apparent from the following description of embodiments.

DESCRIPTION OF EMBODIMENTS

Hereinafter, embodiments of the present invention will be described with reference to the drawings. Although an automatic analysis device that uses a magnetic-particle reagent for analyzing a sample will be exemplarily described below, the type and the like of the reagent are not particularly limited.

Figure 2:
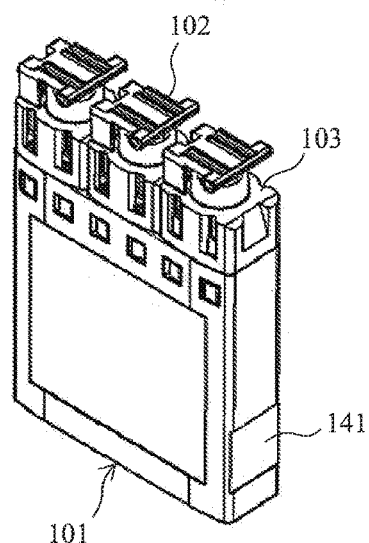
FIG. 2 is a schematic perspective view illustrating a reagent container in a hermetically sealed state.
Figure 3:
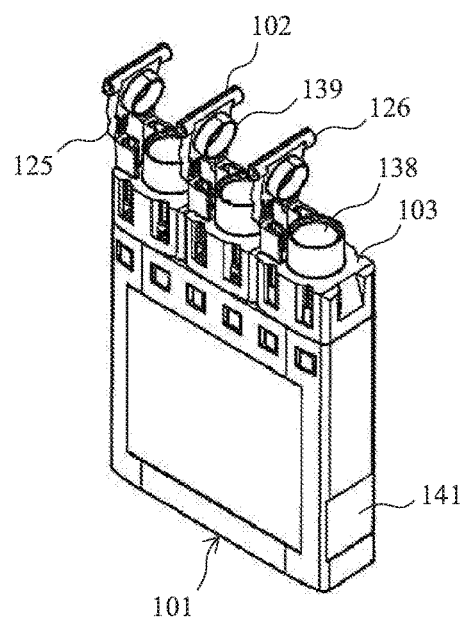
FIG. 3 is a schematic perspective view illustrating a reagent container in an open state.

FIGS. 2 and 3 are schematic perspective views each illustrating an example of a reagent container used in the automatic analysis device of the present invention. The reagent container 101 has a set of three containers, and the set includes, for example, a magnetic-particle solution and two types of reagents. Each container includes a body portion that stores a reagent, an opening 138 through which the reagent can be accessed, and a lid portion 102 that can hermetically seal the opening 138. The outer shape of the entire reagent container 101 is an approximately rectangular parallelepiped with a shoulder portion 103, and the upper side of the shoulder portion has three openings 138 that are arranged side-by-side and protrude upward. In order for the container to be opened or closed by a sample container lid opening/closing unit that is built into the automatic analysis device, the lid portion 102 is provided at its end with a protrusion 126 in a round bar shape, and the protrusion 126 protrudes from the lid portion 102 in the side surface direction of the reagent container 101. In addition, an RFID tag 141 is attached to an end surface of the reagent container 101. A built-in memory of the RFID tag 141 stores a container ID for identifying the reagent container 101, the type of a reagent stored in the reagent container 101, the quantity of the reagent, the expiration date of the reagent, and other necessary information. Although this embodiment illustrates an example in which information on the reagent container 101 is acquired using RFID (Radio Frequency IDentification), it is possible to use not only RFID but also other information reading means such as barcodes.

FIG. 2 is a schematic perspective view illustrating the reagent container in a hermetically sealed state. In the initial state, the opening 138 is hermetically sealed by the lid portion 102. It should be noted that the lid portion is provided with a hermetically sealing member 139, which can hermetically seal the opening 138 by being inserted into the opening 138, in order to reliably seal the opening 138. If the opening 138 is always open, there is a possibility that a reagent in the container may evaporate or the concentration of the reagent may change. Further, if the operator falls down the reagent container 101 by mistake while handling it, there is a possibility that a reagent in the reagent container 101 may be spilt. Such inconvenience can be reduced by hermetically sealing the opening 138 with the lid portion 102 and opening the lid portion 102 when necessary. FIG. 3 is a schematic perspective view illustrating the reagent container in an open state. The lid portion 102 rotates about a hinge 125 as the rotation axis, whereby the lid portion 102 opens from the side of the protruding portion 126. At this time, the hermetically sealing member 139 is completely removed from the opening 138, and the lid portion 102 is opened at a large angle around the hinge 125 as the center.

Figure 4:
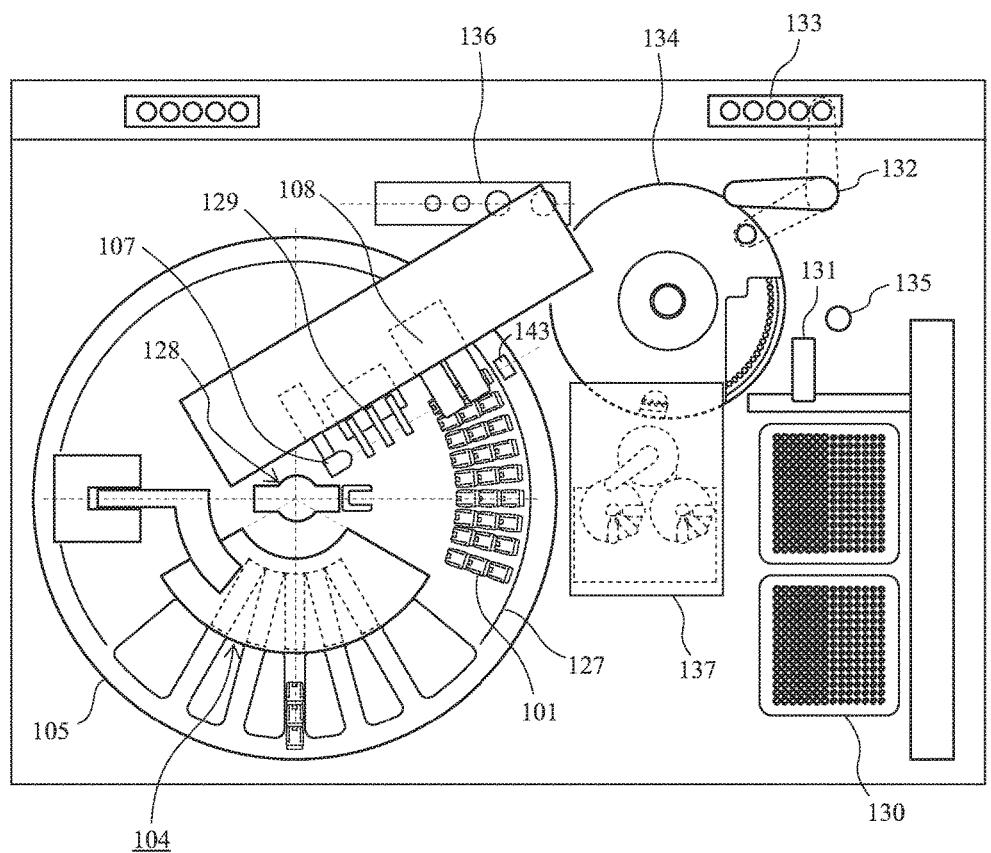
FIG. 4 is a top schematic view illustrating an embodiment of an automatic analysis device in accordance with the present invention.

FIG. 4 is a top schematic view illustrating an embodiment of an automatic analysis device in accordance with the present invention. The automatic analysis device in this embodiment includes a reagent refrigerator 105 with a reagent loader mechanism 104 that automatically transports the reagent container(s) 101 into or out of the device, a magnetic-particle stirring unit 107 that stirs a reagent (in particular, a reagent containing magnetic particles) in the reagent refrigerator, a magazine 130 that holds a plurality of consumable items that are necessary for analyses (e.g., reaction containers and sample dispensing tips), a reaction container/sample dispensing tip transporting unit 131 that transports a consumable item on the magazine 130 to an appropriate position, a sample dispensing unit 132 that dispenses a predetermined quantity of sample from a sample container on a sample rack 133 on the transport line into a reaction container while having a sample dispensing tip mounted thereon, a reaction vessel 134 that holds the reaction container storing the sample at a predetermined temperature, a reagent dispensing unit 108 that sucks a predetermined quantity of reagent in the reagent refrigerator 105 and discharges it into the reaction container; a reaction solution stirring unit 135 that stirs the sample and the reagent in the reaction container for mixing them, a reaction solution washing unit 136 that removes components other than a target component to be measured from the reaction container, and a detection unit 137 for quantitatively measuring the target component to be measured in the reaction solution. The reagent refrigerator 105 is provided with, at a position to be accessed by the reagent dispensing unit 108, an RFID 143 for reading information on a RFID tag, which is attached to the reagent container, in a contactless manner.

The upper surface of the reagent refrigerator 105 is hermetically sealed by a lid (not shown), and a part of the lid is provided with an opening that allows the reagent loader mechanism 104, a stirring rod of the magnetic-particle stirring unit 107, and a probe of the reagent dispensing unit 108 to pass therethrough. In addition, a reagent disk 127, which has a plurality of slots in which reagent containers can be disposed, is provided in the reagent refrigerator 105. Thus, rotationally moving the reagent disk 127 can transport any given reagent container 101 to a position to be accessed by each mechanism. A reagent container moving unit 128 can move the reagent container 101 between the reagent loader mechanism 104, a slot of the reagent disk 127, and the stirring position of the magnetic-particle stirring unit 107. In addition, a reagent container lid opening/closing unit 129 can open the lid of the reagent container 101 at an appropriate timing before processing is performed with the magnetic-particle stirring unit 107 or the reagent dispensing unit 108, and can, upon termination of the processing, close the lid after the reagent is used.

As a preparation to start analysis, the reagent container 101 to be used for analysis is first disposed on the reagent disk 127 in the reagent refrigerator 105. The operator inserts the reagent container 101 into the reagent loader mechanism 104. After that, the reagent loader mechanism 104 is lowered so that it is returned into the reagent refrigerator 105, and then, the reagent container 101 disposed on the reagent loader mechanism 104 is moved to a slot of the reagent disk 127 by the reagent container moving device 128. The reagent container 101 moved to the reagent disk 127 is used for an analysis process. The operation of moving the reagent loader mechanism 104 up and down may be performed on a screen for operating the automatic analysis device or operating a switch that is provided around the reagent loader mechanism 104. The details of the reagent loader mechanism 104 and the method for inserting the reagent container 101 into the reagent loader mechanism 104 will be described below.

An analysis process is started upon completion of the loading of the reagent container 101 that is necessary for analysis. The analysis process is automatically executed in accordance with predetermined procedures under the control of a host computer. For example, a reaction container disposed on the magazine 130 is transported into the reaction vessel 134 by the reaction container/sample dispensing tip transporting unit 131, and further, a sample dispensing tip is transported to a position where the tip is to be mounted on the tip end of the probe of the sample dispensing unit 132. The reaction vessel 134 can be rotationally driven in the horizontal direction while holding a plurality of reaction containers. Once the reaction vessel 134 is rotated to reach a reagent dispensing position, a determined quantity of reagent is first dispensed into the reaction container from the reagent container 101 by the reagent dispensing unit 108. At this time, the host computer communicates with the RFID 143 that has read information on the RFID tag 141 attached to the reagent container 101, and confirms that the reagent to be dispensed into the reaction container is a desired reagent. At the same time, the sample dispensing unit 132 having the sample dispensing tip mounted thereon sucks a sample from a sample container mounted on the sample rack 133, and the reaction container, which contains the reagent dispensed thereinto, is moved to a sample dispensing position through rotation of the reaction vessel 134, so that the sample is dispensed into the reaction container by the sample dispensing unit 132. After that, the reaction container containing the reagent and the sample is kept warm on the reaction vessel 134 for a given period of time so as to cause reaction between the reagent and the sample in the reaction container. After that, the reaction container is moved to the reagent dispensing position again so that magnetic particles in the reagent container 101 are dispensed into the reaction container by the reagent dispensing unit 108. Then, after the reaction vessel 134 has rotated, the reaction container on the reaction vessel 134 is moved to the reaction solution stirring unit 135 by the reaction container/sample dispensing tip transporting unit 131 so that the magnetic particles as well as the reagent and the sample that have reacted for a given period of time in the reaction container are stirred by the reaction solution stirring unit 135. The reaction container in which stirring has terminated is returned to the reaction vessel 134 again by the reaction container/sample dispensing tip transporting unit 131, and further, reaction is caused to occur on the reaction vessel 134 for a given period of time. Then, the resulting reaction solution (reagent/sample/magnetic particles) in the reaction container is introduced into the detection unit 137 to perform detection. Herein, depending on the items to be analyzed, a process of washing the reaction solution may be performed with the reaction solution washing unit 136 before the detection process in order to remove impurities contained in the reaction solution. A series of such processes can be performed successively. The host computer displays the type, the residual amount, expiration date, and the like of a reagent held in each reagent container in the reagent refrigerator 105, and displays a warning about addition of a reagent or replacement of the reagent with a new one at an appropriate timing.

The automatic analysis device in this embodiment performs analysis by mounting the reagent container 101, which stores a reagent, into the reagent refrigerator 105 with a refrigeration function. Transport of the reagent container 101 into and out of the reagent refrigerator 105 is performed with the reagent loader mechanism 104 that can have a plurality of sets of reagent containers 101 mounted thereon. The reagent refrigerator 105 includes therein the reagent disk 127 that can rotate while having a plurality of sets of reagent containers 101 mounted thereon, the reagent container moving unit 128 that can move the reagent containers 101 between the reagent loader mechanism 104 and the reagent disk 127, the reagent container lid opening/closing unit 129 that can open or close the lid portion 102 of each reagent container 101 during an analysis process, and the like. The magnetic-particle stirring unit 107, the reagent dispensing unit 108, and the like are provided outside the reagent refrigerator 105, and such units can access the inside of each reagent container 101 mounted on the reagent disk 127 at the position of the opening provided in the lid that covers the upper portion of the reagent refrigerator 105.

The reagent disk 127 can be rotationally driven in the horizontal direction, and moves the reagent container 101 mounted thereon to a position where stirring and dispensing are to be performed during an analysis process, and then, the lid portion 102 of the reagent container 101 is opened with the reagent container lid opening/closing unit 129 so that the magnetic particles in the reagent container 101 are stirred with the magnetic-particle stirring unit 107 and the reagent stored in the reagent container 101 is dispensed with the reagent dispensing unit 108. The lid portion 102 of the reagent container 101 in which stirring of magnetic particles and dispensing of the reagent have terminated is closed by the reagent container lid opening/closing unit 129. The process and operation of each unit in the automatic analysis device are performed under the control of the host computer.

Figure 1:
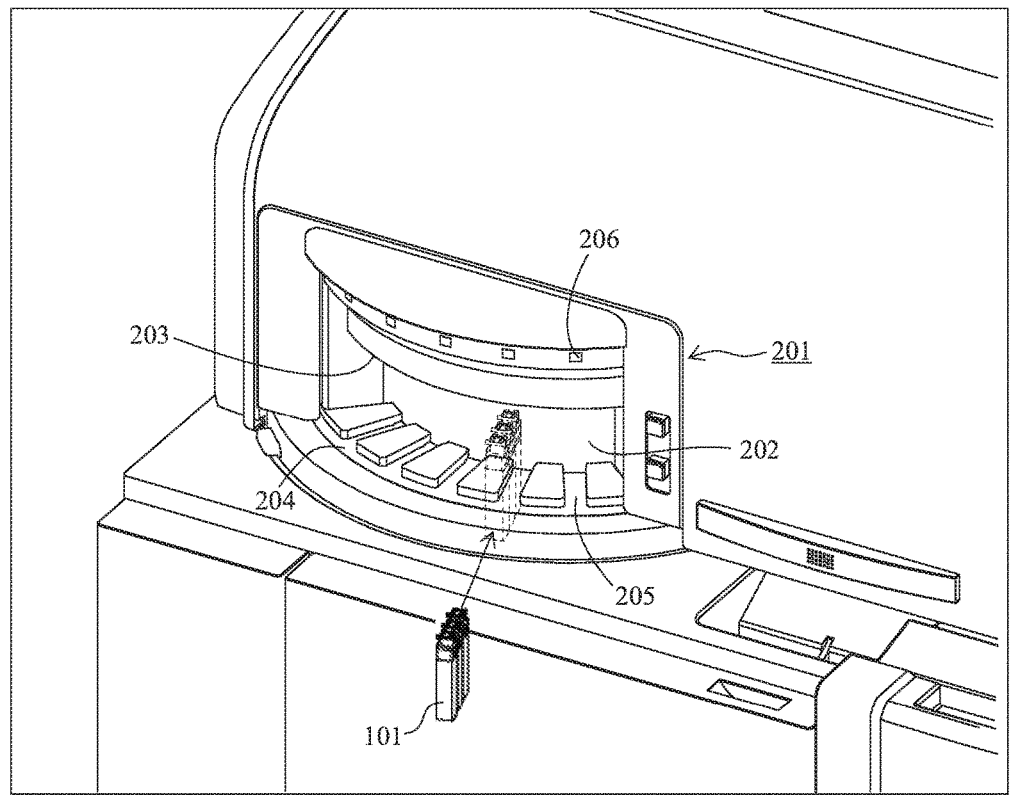
FIG. 1 is a schematic view illustrating an example of a reagent container loading portion of an automatic analysis device.

FIG. 1 is a schematic view illustrating an example of a reagent container loading portion of the automatic analysis device. The reagent container 101 is transported into the reagent refrigerator 105 in the automatic analysis device via a reagent container loading portion 201.

The reagent container loading portion 201 in this embodiment includes an opening 202 through which reagent containers are introduced into the device, and an approach region that is formed by a space between an upper surface 203 and a lower surface 204 connecting to the opening 202 in front of the opening. The reagent loader mechanism 104, which holds the reagent containers 101 and transports them into the reagent refrigerator 105 of the automatic analysis device, is disposed in the body of the device on the inner side than the opening 202, and does not appear in FIG. 1. FIG. 1 illustrates a state in which the opening 202 is blocked by a shielding member of a reagent container transport tool of the reagent loader mechanism 104 as described below. In this embodiment, a plurality of guide grooves 205 for guiding reagent containers is arranged radially on the lower surface connecting to the opening 202 in front of the opening. The guide grooves 205 are each adapted to guide the reagent container 101 toward the inside of the opening 202 by sliding the lower end of the reagent container 101 in the guide groove 205. In this example, five guide grooves are provided along the direction to insert the reagent containers. A display lamp 206 indicating a state is provided above each guide groove on the upper portion of the front surface of the reagent container loading portion.

Figure 5:
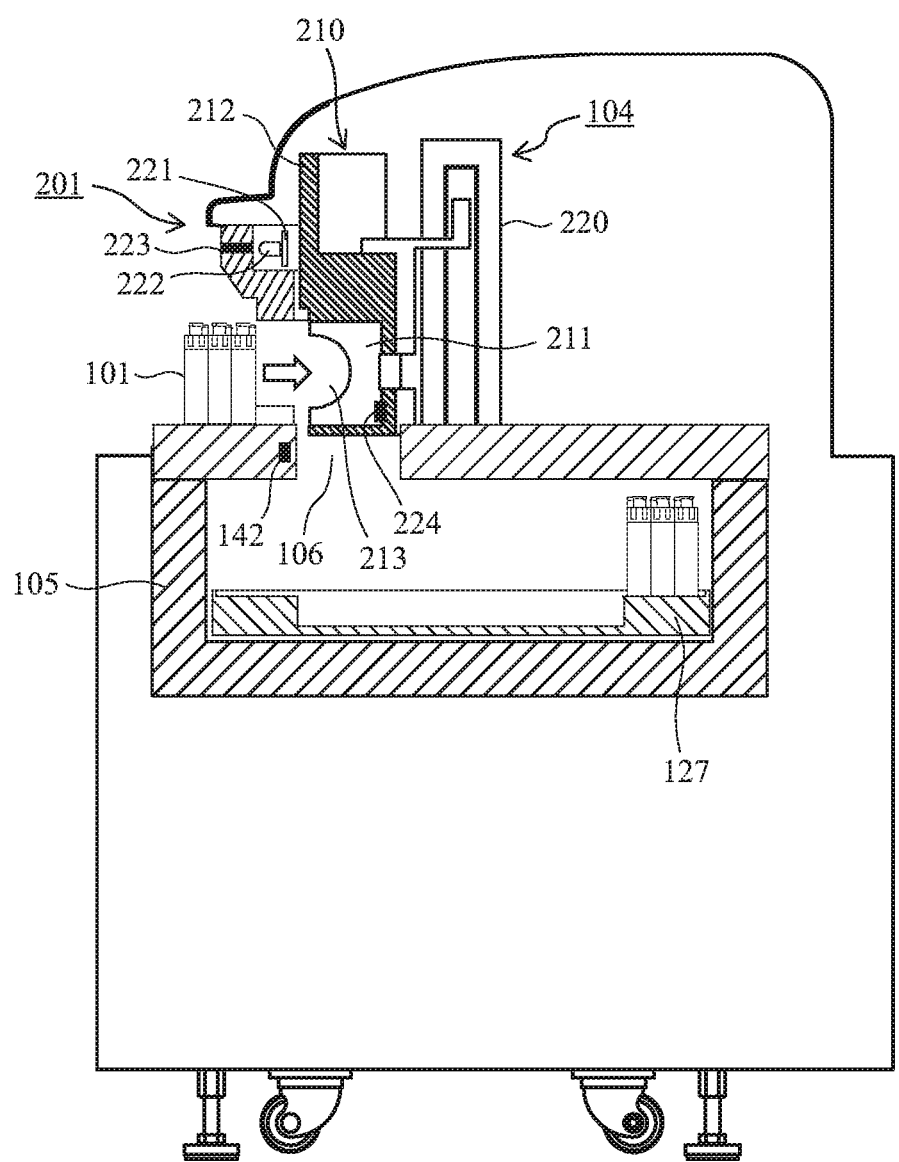
FIG. 5 is a schematic cross-sectional view of the automatic analysis device when a reagent container transport tool of a reagent loader mechanism is at an elevated position.
Figure 6:
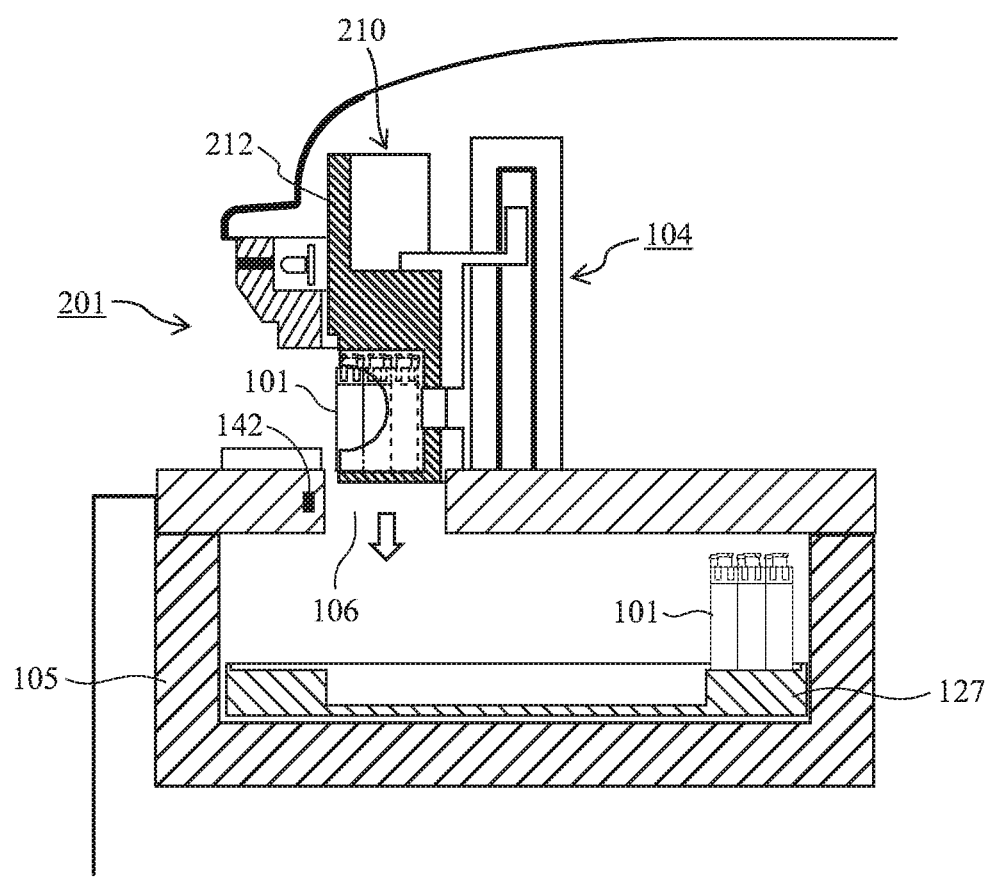
FIG. 6 is a schematic cross-sectional view of the automatic analysis device when the reagent container transport tool of the reagent loader mechanism is at an elevated position.
Figure 7:
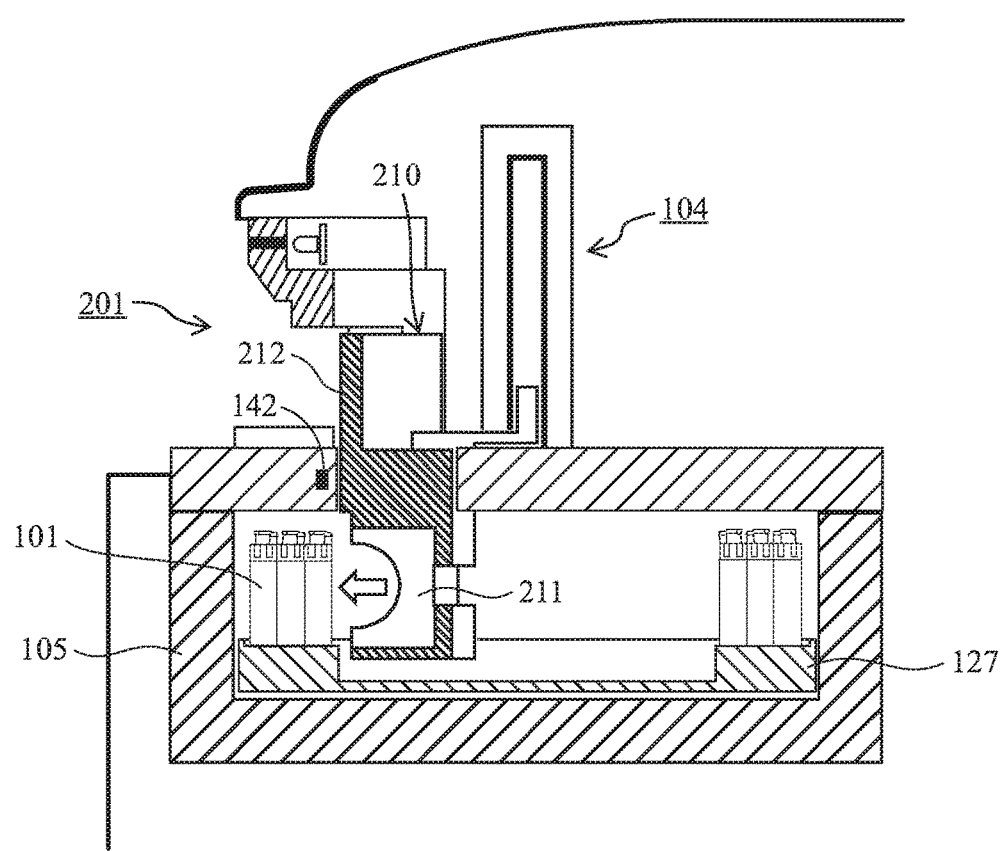
FIG. 7 is a schematic cross-sectional view of the automatic analysis device when the reagent container transport tool of the reagent loader mechanism is at a lowered position.

FIGS. 5 to 7 are schematic cross-sectional views each illustrating the procedures to transport reagent containers to the automatic analysis device in this embodiment. Each of FIGS. 5 to 7 illustrates the approach region in front of the opening of the reagent container loading portion, the reagent loader mechanism 104, and the reagent refrigerator 105. The procedures to transport reagent containers into the reagent refrigerator from the opening of the reagent container loading portion will be described with reference to the drawings.

Figure 8:
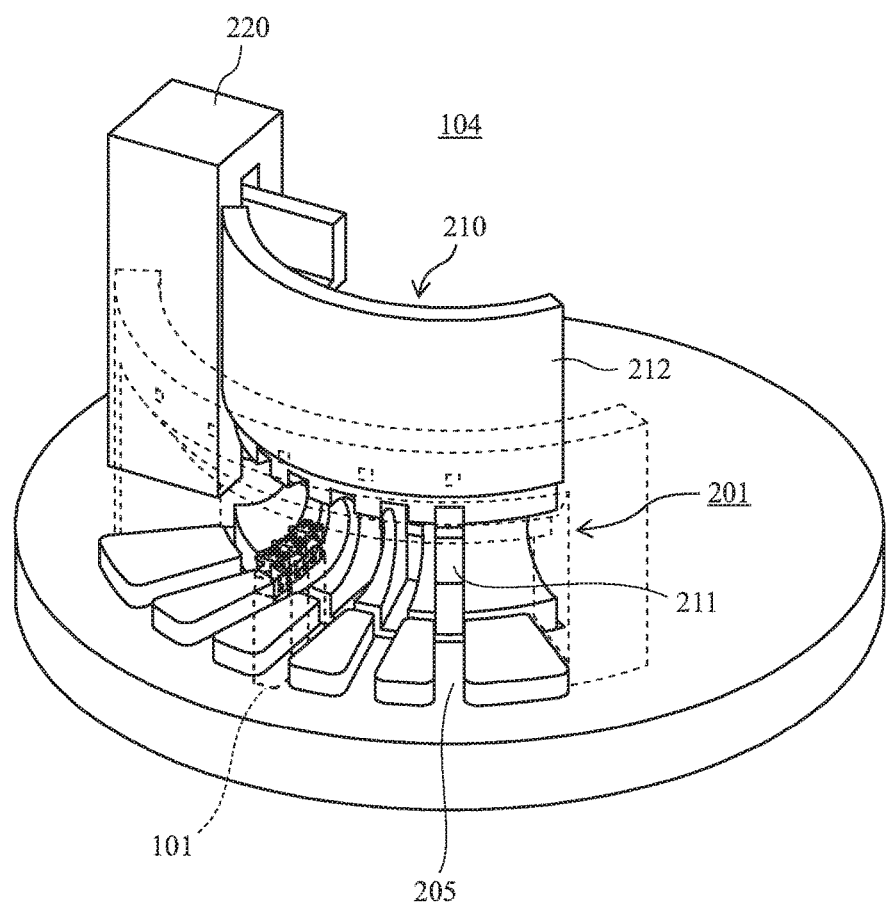
FIG. 8 is a schematic view illustrating a state in which the reagent container transport tool of the reagent loader mechanism is at an elevated position.

FIG. 5 is a schematic cross-sectional view of the automatic analysis device when a reagent container transport tool 210 of the reagent loader mechanism 104 is at an elevated position. The reagent loader mechanism 104 has the reagent container transport tool 210, which is movable up and down, and an elevating and lowering mechanism 220 that elevates or lowers the reagent container transport tool. The reagent container transport tool 210 has, as illustrated in FIG. 8, a plurality of (5 in this embodiment) reagent container insertion slots 211 arranged radially thereon, and also has a shielding member 212 with an L-shaped cross-section above the slots 211. The reagent container transport tool 210 is movable between an elevated position illustrated in FIG. 5 and a lowered position illustrated in FIG. 7 by the elevating and lowering mechanism 220. The reagent refrigerator 105 has in its upper portion an opening 106 that allows the reagent container transport tool 210 to pass therethrough, and has the rotatable reagent disk 127 inside. The reagent disk 127 has an annular reagent container mount region on its outer peripheral side. The opening 106 is provided on its side surface with an RFID 142.

As the reagent container transport tool 210 is elevated, the shielding member 212 provided above the slots 211 moves to a portion above the opening 202 of the reagent container loading portion 201, and thus opens the opening 202. In other words, the automatic analysis device in this embodiment has an evacuation space for storing the shielding member 212 that is evacuated from the opening of the reagent container loading portion, above the reagent container transport tool 210. Meanwhile, in such a state, the opening 106 provided in the reagent refrigerator 105 is not blocked by the reagent container transport tool 210 and thus is open. In a state in which the reagent container transport tool 210 is elevated by the elevating and lowering mechanism 220, the guide grooves 205 of the reagent container loading portion 201 communicate with the respective slots 211 of the reagent container transport tool 210. Thus, the operator can, by sliding a reagent container(s) along the guide groove(s) 205 while gripping the reagent container(s) with one hand up to the position of the reagent container transport tool 210 of the reagent loader mechanism 104, reliably insert the reagent container(s) into the slogs) 211. A sidewall of the reagent container transport tool 210 that forms the slots 211 is partially cut out so that a hand or finger of the operator who inserts a reagent container(s) into the slogs) while gripping the reagent container(s) will not touch the sidewall. Such a cutout 213 is provided at a portion corresponding to the hand of the operator who grips a reagent container(s). Thus, the operator can safely and reliably mount a reagent container(s) into the slot(s) 211 of the reagent container transport tool 210 while his/hand, which is gripping the reagent container(s), is not interrupted by the walls forming the slots. That is, providing the cutout 213 makes it easier to put a finger into the reagent container transport tool 210, and thus makes it easier to insert a reagent container(s) into the slot(s) or take out the reagent container(s) from the slot(s).

In this embodiment, the reagent container transport tool 210 of the reagent loader mechanism has five slots that is the same number as the number of the guide grooves 205 provided on the reagent container loading portion 201 so that five reagent containers are allowed to be held radially in the slots. However, there may be cases where the width of each slot is almost the same as the width of each reagent container, leaving no clearance, and thus the inside cannot be sufficiently seen. In such cases, it is difficult to promptly and reliably insert a reagent container(s) into the slot(s) of the reagent container transport tool without the guide grooves on the reagent container loading portion. Further, providing the radially arranged guide grooves can, when a plurality of reagent containers is inserted into the grooves while being gripped with a hand, prevent mutual interference between the reagent containers and thus can prevent unintended falling of the reagent containers and spills.

In this embodiment, the display lamp 206 is formed by guiding light from an LED 222 held on the substrate 221, which is provided on the rear surface of the reagent container loading portion 201, to the front surface of the upper portion of the reagent container loading portion 201 using a light guiding member 223. Needless to say, it is also possible to omit the light guiding member by exposing the LED to the front surface of the upper portion of the reagent container loading portion 201. When the reagent container transport tool 210 is at an elevated position as described above, arranging the substrate 221 such that it is opposite the shielding member 212 can allow heat, which is generated from the substrate 221, to be confined in a small space by the shielding member 211. Thus, there is no possibility that the heat will adversely affect the reagent refrigerator 105 that is not in a hermetically sealed state.

It is also possible to provide a touch sensor 224 on the innermost wall, which is adapted to be in contact with the reagent container 101, of each reagent container insertion slot 211 of the reagent container transport tool 210. If the operator leaves the reagent container 101 that is not completely inserted into the slot 211 of the reagent container transport tool 210, and the reagent container transport tool 210 is lowered in such a state, the reagent container 101 is sandwiched between the neighboring members, and thus, the following process is interrupted or the members may become damaged, which is problematic. The touch sensor 224 is provided to address such a problem. When the reagent container 101 inserted into the slot 211 contacts the contact sensor 224, the LED 222, that is, the display lamp 206 corresponding to the load position is lit to inform the operator of the contact. The operator can, by pressing the reagent container 101 into the slot of the reagent container transport tool 210 until the display lamp 206 is lit, confirm that the reagent container has been completely inserted.

FIG. 6 is a schematic cross-sectional view of the automatic analysis device when the reagent container transport tool 210 of the reagent loader mechanism 104 is at an elevated position as in FIG. 5. FIG. 6 illustrates a state in which insertion of the reagent container 101 that is necessary for the reagent container transport tool 210 of the reagent loader mechanism 140 is complete. As illustrated in FIG. 6, the reagent container 101 is completely inserted into the slot of the reagent container transport tool 210. Providing the guide grooves 205 on the reagent container loading portion 201 and providing the cutout 213 in the slots 211 allows the operator to easily and reliably perform an operation of inserting the reagent container(s) 101 into the reagent container transport tool 210 of the reagent loader mechanism 104. Next, the reagent container transport tool 210 is lowered to the inside of the reagent refrigerator 105 through the opening 106 in the upper portion of the reagent refrigerator 105 by the elevating and lowering mechanism 220. While the reagent container transport tool 210 is lowered through the opening 106, information on the RFID tag of the reagent container 101, which is inserted into the reagent container transport tool 210, is read by the RFID 142.

FIG. 7 is a schematic cross-sectional view of the automatic analysis device when the reagent container transport tool 210 of the reagent loader mechanism 104 is at a lowered position. When the reagent container transport tool 210 is moved to a lowered position by the elevating and lowering mechanism 220, the slot 211, which holds the reagent container, of the reagent container transport tool 210 is located in the reagent refrigerator 105. In such a state, a space that is created above the shielding member 212 of the reagent container transport tool 210 is an evacuation space to store the shielding member 212 that is evacuated from the opening 202 of the reagent container loading portion. At this time, the vertical portion of the shielding member 212 of the reagent container transport tool 210 blocks the opening 202 of the reagent container loading portion 201, and realizes an inaccessible state illustrated in FIG. 1. Meanwhile, when the reagent container transport tool 210 is at a lowered position, the horizontal portion of the shielding member 212 blocks the opening 106 in the upper portion of the reagent refrigerator 105. That is, in a state in which the reagent container transport tool 210 of the reagent loader mechanism 104 is located at the lowermost position, the reagent refrigerator 105 can be adapted to be hermetically sealed so as to prevent unwanted access to the inside of the device from the reagent container loading portion 201, improve the cooling efficiency of the reagent refrigerator 105, and prevent mixing of debris and dust. It should be noted that as the guide grooves 205 are arranged radially on the reagent container loading portion 201, blocking the opening 202 on the central side of the radial shape as in this embodiment can reduce the area to block the opening more than when a door is provided outside the guide grooves 205 to block the opening 202, and thus can omit the member, which contributes to reducing the cost.

After that, the reagent container 101 inserted into the slot 211 of the reagent container transport tool 210 is moved to the reagent disk 127 by the reagent container moving unit 128. The reagent container moving unit 128 can be implemented using a known technique. For example, the reagent container moving unit 128 illustrated in FIG. 4 includes a gripping portion that grips a reagent container by sandwiching it from the side surfaces thereof, and a telescopic portion that moves the gripping portion in the radius direction, and is adapted to transfer the reagent container between the slot 211 of the reagent container transport tool 210 of the reagent loader mechanism 104 and the slot of the reagent disk 127.

When the reagent container 101 is discharged from the device, reverse procedures to those illustrated in FIGS. 5 to 7 are executed. First, the reagent container 101 to be discharged is moved to the slot 211 of the reagent container transport tool 210 of the reagent loader mechanism 104 using the reagent container moving unit 128 in the reagent refrigerator 105. After that, the reagent loader mechanism 104 is elevated so that the operator inserts his/her hand from the opening of the reagent container loading portion 201 to grip the reagent container 101 mounted in the slot 211 of the reagent container transport tool 210 of the reagent loader mechanism 104 and take it to the outside of the device.

As illustrated in FIGS. 5 to 7, the slots of the reagent container mount region on the reagent disk 127 are disposed on the outer peripheral side of the circular disk, and the reagent container transport tool 210 of the reagent loader mechanism 104 is lowered to the inner side than the reagent container mount region of the reagent disk 127. Thus, a reagent container that is delivered from the slot of the reagent container transport tool 210 to the reagent disk 127 in the reagent refrigerator 105 is moved from the central side to the outer peripheral side along the radial direction of the reagent disk 127. Therefore, a reagent container to be stored into the reagent refrigerator from the outside via the reagent container loading portion of the automatic analysis device is guided into the reagent refrigerator along a U-shaped movement path including a horizontal movement in which the reagent container is inserted into the slot of the reagent container transport tool of the reagent loader mechanism 104 along the radial guide groove (FIG. 5), a vertical movement along with the lowering of the reagent container transport tool by the elevating and lowering mechanism (FIG. 6), and a horizontal movement in which the reagent container is moved to the outer peripheral region of the reagent disk from the slot of the reagent container transport tool of the reagent loader mechanism (FIG. 7). When a reagent container is stored along a U-shaped movement path as described above, the reagent container can be stored in a compact manner without requiring a large space.

Figure 9:
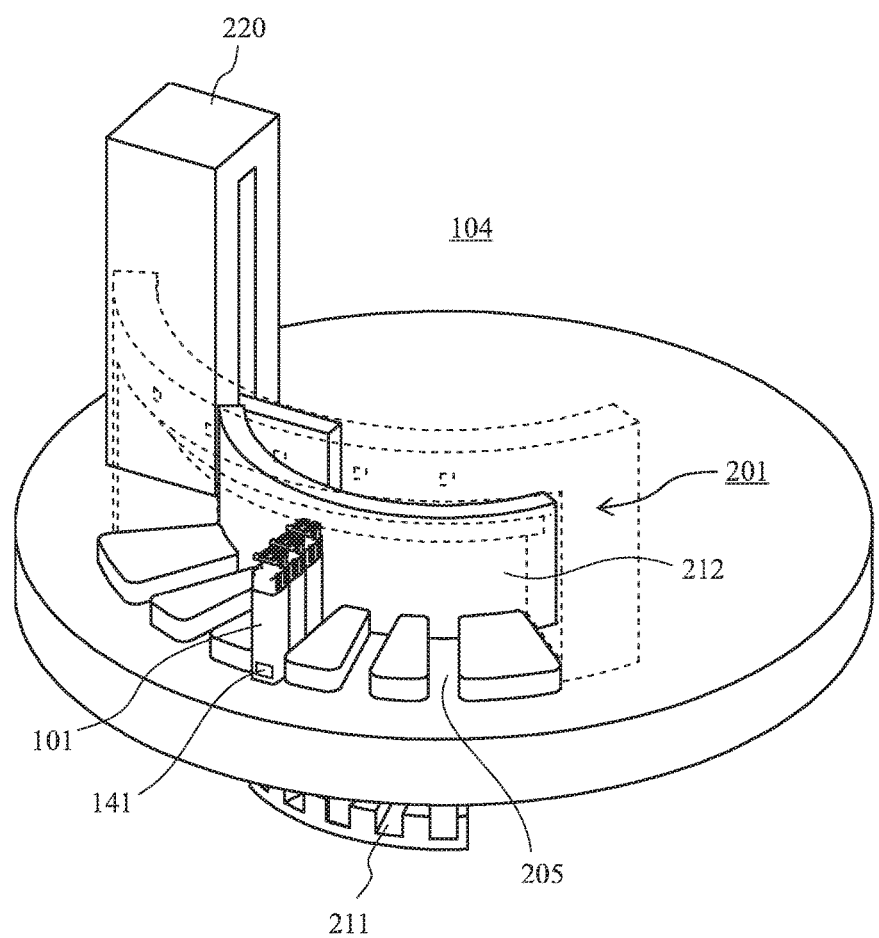
FIG. 9 is a schematic view illustrating a state in which the reagent container transport tool of the reagent loader mechanism is at a lowered position.

FIGS. 8 and 9 are schematic views each illustrating the relationship between the entire reagent loader mechanism and the guiding portion. In order to clearly illustrate the entire reagent loader mechanism, the mechanism is shown with the surrounding structure removed for purposes of simplicity. FIG. 8 corresponds to FIG. 5, and is a schematic view illustrating a state in which the reagent container transport tool of the reagent loader mechanism is at an elevated position. FIG. 9 corresponds to FIG. 7, and is a schematic view illustrating a state in which the reagent container transport tool of the reagent loader mechanism is at a lowered position.

The reagent container transport tool 210 has five reagent container insertion slots 211, which is the same number as the number of the guide grooves 205. When the reagent container transport tool 210 of the reagent loader mechanism 104 is at an elevated position, the reagent container insertion slots 211 of the reagent container transport tool 210 are exposed in the opening 202 of the reagent container loading portion 201 as illustrated in FIG. 8 so that the reagent container(s) 101 can be inserted into the slot(s) 211 of the reagent container transport tool 210 along the guide groove(s) 205. As illustrated in FIG. 8, the five radially arranged guide grooves 205 communicate with the five radially arranged slots of the reagent container transport tool 210, respectively. That is, the radially arranged slots 211 and the radially arranged guide grooves 205 are completely continuous with one another and form grooves in integrated radial shapes. In addition, a sidewall of the reagent container transport tool 210 that forms the slots is partially cut out on a side that faces the operator so that a hand of the operator who grips a reagent container(s) will not touch the sidewall. Thus, the operator who is gripping a reagent container(s) to be inserted into the slot(s) with one hand can, only by putting the bottom portion(s) of the reagent container(s) into the guide groove(s) 205 and sliding the reagent container(s) toward the rear of the opening 202 along the guide groove(s) 205 while gripping the reagent container(s), safely and reliably insert the reagent container(s) into the slot(s) 211.

In this embodiment, the reagent container loading portion is formed in an arcuate shape. Along with this, the region of the guide grooves 205 arranged on the reagent container loading portion 201 as well as the opening 202 is also formed in an arcuate shape, and the surface of the shielding member 212 that is provided on the reagent container transport tool 210 to block the opening 202 is a cylindrical surface.

When the reagent container transport tool 210 of the reagent loader mechanism 104 is lowered, the shielding member 212 provided on the reagent container transport tool 210 is also lowered to the position of the opening 202 of the reagent container loading portion from the evacuation space in the upper portion, thereby blocking the opening 202 as illustrated in FIG. 9. At this time, the shielding member 212 also blocks the opening in the upper portion of the reagent refrigerator 105 to put it in a hermetically sealed state.

Figure 10:
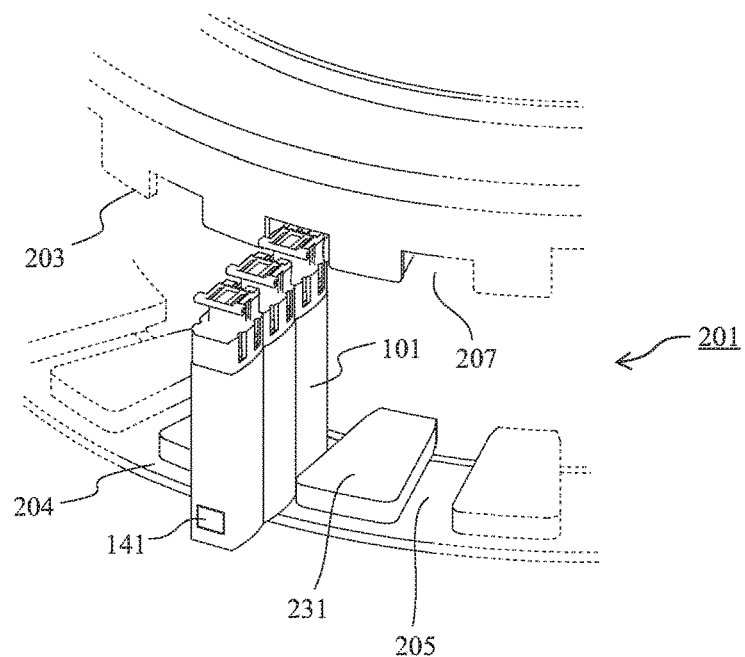
FIG. 10 is a schematic view illustrating another example of guide grooves provided on the reagent container loading portion.

FIG. 10 is a schematic view illustrating another example of the guide grooves provided on the reagent container loading portion. In this embodiment, not only a plurality of guide grooves 205, which is adapted to guide a reagent container, is arranged radially on the lower surface 204 of the approach region in front of the opening provided in the reagent container loading portion 201, but also guide grooves 207, which are opposite the guide grooves 205 on the lower surface, are arranged radially on the upper surface 203 of the approach region. As the reagent container 101 slides with its upper and lower ends fixed on the upper and lower guide grooves 207 and 205 provided in the approach region, the reagent container 101 can be inserted into the slot of the reagent container transport tool 210 with higher accuracy. It should be noted that in this embodiment, the guide grooves 205 provided on the lower surface of the reagent container loading portion 201 have a configuration in which a plurality of projecting members 231 is provided on the base plane, and spaces between the projecting members are used as the guide grooves. The planar shape of each projecting member 231 is approximately trapezoidal.

Figure 11:
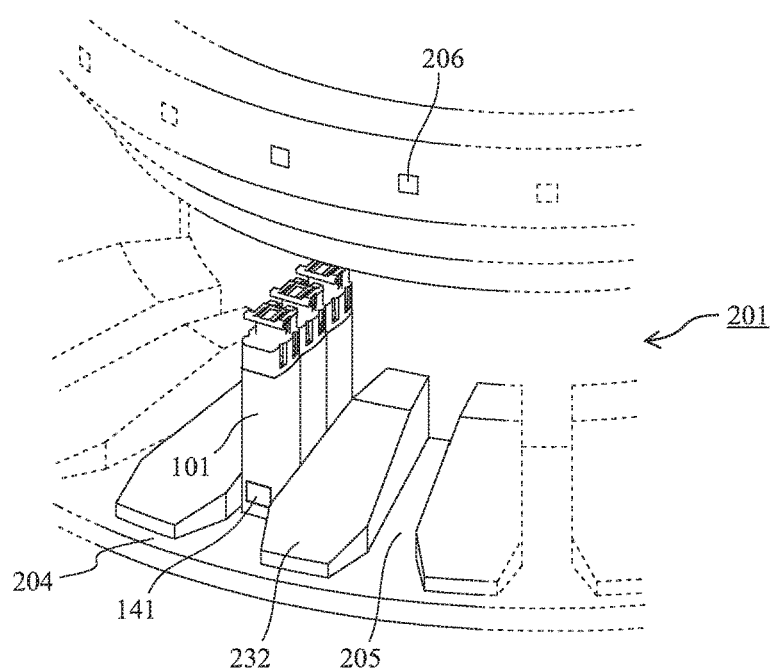
FIG. 11 is a schematic view illustrating another example of guide grooves provided on the reagent container loading portion.

FIG. 11 is a schematic view illustrating another example of the guide grooves provided on the reagent container loading portion. In this embodiment, each of the guide grooves 205 that are arranged radially on the lower surface 204 of the approach region in front of the opening of the reagent container loading portion 201 has a shape in which the width on the front entrance side is wider and the width of the following portion is constant, and a reagent container is adapted to be guided to a higher position on the rearer side. In the case of the guide grooves 205 in this embodiment, as the width on the front entrance side is wider, the reagent container 101 can be smoothly inserted when it is first inserted into the guide groove 205. Further, as each groove is deeper on the rearer side, the reagent container 101 is more securely fixed in the guide groove 205 on the rearer side, thus reducing rattling. This allows the reagent container to be more smoothly inserted into the slot of the reagent container transport tool. The guide grooves 205 in this embodiment also have a configuration in which a plurality of projecting members 232 is arranged on the base plane, and spaces between the projecting members are used as the guide grooves. The planar shape of each projecting member 232 is a shape obtained by chamfering the corners of a trapezoid on the front side, and is a shape in which the projecting member 232 is higher on the rear side than on the front side.

Figure 12:
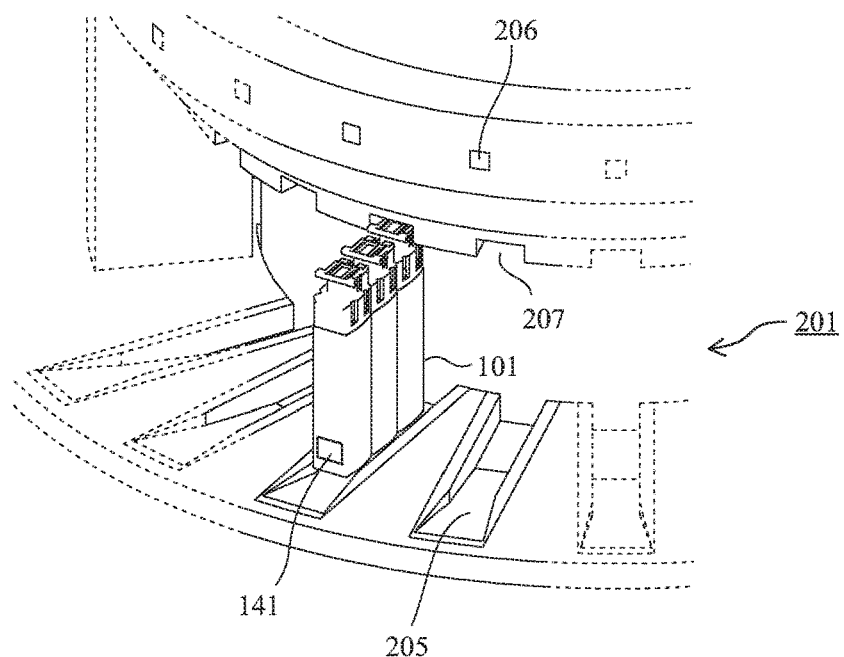
FIG. 12 is a schematic view illustrating another example of guide grooves provided on the reagent container loading portion.

FIG. 12 is a schematic view illustrating another example of the guide grooves provided on the reagent container loading portion. In this embodiment, guide grooves 205 and 207 are arranged radially on the upper surface and lower surface of the approach region in front of the opening of the reagent container loading portion 201. The guide grooves 205 provided on the lower surface of the reagent container loading portion in this embodiment have a configuration in which grooves obtained by forming recesses in the base plane are used as the guide grooves. Each guide groove 205 has a shape in which the width on the front side is wider so that the reagent container 101 can be smoothly inserted when it is first inserted into the guide groove 205. In addition, as each guide groove 205 is formed such that the depth gradually becomes greater from the base plane, a hand will not touch a portion between the grooves when inserted.

Figure 13:
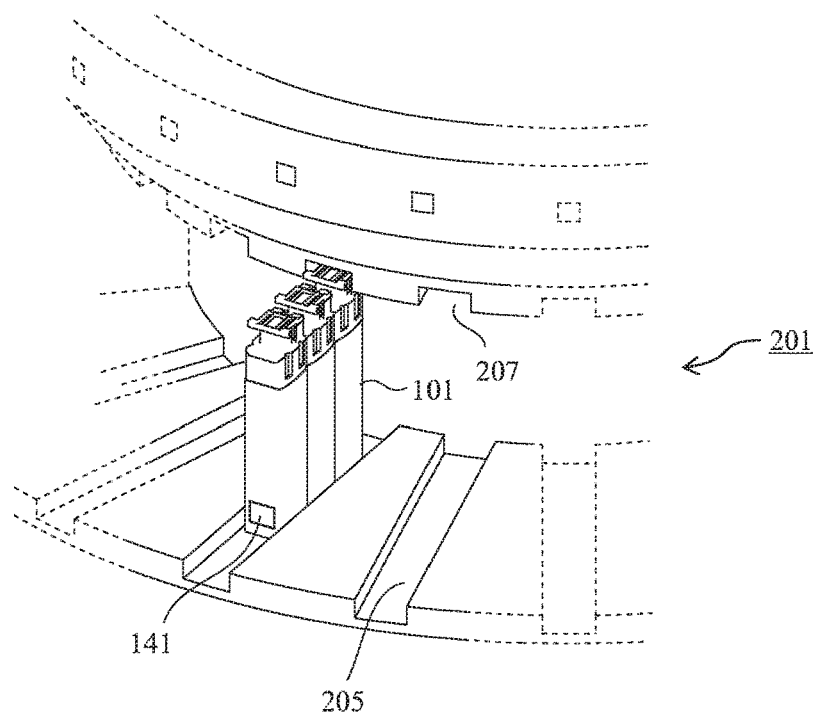
FIG. 13 is a schematic view illustrating another example of guide grooves provided on the reagent container loading portion.

FIG. 13 is a schematic view illustrating another example of the guide grooves provided on the reagent container loading portion. In this embodiment, guide grooves 205 and 207 are arranged radially on the upper surface and lower surface of the approach region in front of the opening of the reagent container loading portion 201. In addition, shown herein is an example in which the guide grooves 205 start from an end of the lower surface provided on the reagent container loading portion 201.

In the reagent loader mechanism 104 in the aforementioned embodiments, five slots 211 are provided on the reagent container transport tool 210 so that a maximum of five reagent containers 101 can be loaded or discharged through one operation. However, it is not necessarily required to dispose reagent containers in all of the slots, and less than five reagent containers can be loaded or discharged. Alternatively, the reagent container transport tool 210 of the reagent loader mechanism 104 may have a configuration in which less than five or more than five reagent containers can be mounted thereon.

It should be noted that the present invention is not limited to the aforementioned embodiments, and includes a variety of variations. For example, although the aforementioned embodiments have been described in detail to clearly illustrate the present invention, the present invention need not include all of the configurations described in the embodiments. It is possible to replace a part of a configuration of an embodiment with a configuration of another embodiment. In addition, it is also possible to add, to a configuration of an embodiment, a configuration of another embodiment. Further, it is also possible to, for a part of a configuration of each embodiment, add, remove, or substitute a configuration of another embodiment.

REFERENCE SIGNS LIST

101 Reagent container
104 Reagent loader mechanism
105 Reagent refrigerator
127 Reagent disk
201 Reagent container loading portion
202 Opening
205 Guide groove
206 Display lamp
207 Guide groove
210 Reagent container transport tool
211 Slot
212 Shielding member
213 Cutout
220 Elevating and lowering mechanism
221 Substrate
222 LED
223 Light guide

The invention claimed is:

1. An automatic analysis device comprising:
a housing including a reagent container loading portion that defines a first opening through which a reagent container which contains a reagent is introduced;
a refrigerator arranged in the housing and having an upper surface that defines a second opening;
a reagent container transport tool having a plurality of reagent container insertion slots which are arranged radially, and a shielding member having an L-shaped cross-section arranged above the slots;
an elevating and lowering mechanism configured to elevate and lower the reagent container transport tool up and down through the second opening; and
a detector configured to measure a target component in a reaction container which contains the reagent and a sample,
wherein:
the reagent container loading portion has a lower surface which defines the first opening and a plurality of first guide grooves which are arranged radially on the lower surface in front of the first opening, each of the guide grooves configured to guide the reagent container through the first opening,
in a state where the reagent container transport tool is at an elevated position and the plurality of reagent container insertion slots are at the first opening, the plurality of first guide grooves respectively communicate with the reagent container insertion slots of the reagent container transport tool, and each of the guide grooves is configured to guide the reagent container through the first opening to a respective one of the respective reagent container insertion slots, and in a state where the reagent container transport tool is at a lowered position and the plurality of reagent container insertion slots are in the refrigerator, the shielding member blocks the first opening.

2. The automatic analysis device according to claim 1, wherein:

in the state where the reagent container transport tool is at the lowered position and the plurality of reagent container insertion slots are in the refrigerator, the shielding member blocks the second opening.

3. The automatic analysis device according to claim 1, wherein:

in the state where the reagent container transport tool is at the elevated position and the plurality of reagent container insertion slots are at the first opening, the shielding member is arranged in an evacuation space above the first opening.

4. The automatic analysis device according to claim 1, wherein:

a surface of the shielding member that blocks the first opening is a cylindrical surface.

5. The automatic analysis device according to claim 1, wherein:

the reagent container loading portion has an upper surface which defines the first opening and a plurality of second guide grooves which are arranged radially on the upper surface in front of the first opening, and the second guide grooves are respectively opposite the first guide grooves arranged on the lower surface.

6. The automatic analysis device according to claim 1, further comprising:

a plurality of display lamps provided on an upper portion of a front surface of the reagent container loading portion, the plurality of display lamps corresponding to the respective guide grooves.

7. The automatic analysis device according to claim 6, further comprising:

a substrate provided on a rear surface of the reagent container loading portion, the substrate holding the display lamps, wherein:

in the state where the reagent container transport tool is at the elevated position and the plurality of reagent container insertion slots are at the first opening, the substrate is located opposite the shielding member.

8. The automatic analysis device according to claim 1, wherein:

the reagent container insertion slots are defined by a plurality of sidewalls having cutouts.

9. The automatic analysis device according to claim 1, wherein:

the refrigerator includes therein a rotatable reagent disk, the rotatable reagent disk having a reagent container mount region on an outer peripheral side, and a reagent container moving device, in the state where the reagent container transport tool is at the lowered position and the plurality of reagent container insertion slots are in the refrigerator, the reagent container insertion slots are at an inner side of the reagent disk relative to the outer peripheral side, and the reagent container moving device is configured to move the reagent container from one of the reagent container insertion slots to the reagent container mount region of the reagent disk.

* * * * *